(12) United States Patent
Pagel et al.

(10) Patent No.: US 8,114,048 B2
(45) Date of Patent: Feb. 14, 2012

(54) BALLOON CATHETER WITH ELASTIC SEGMENT

(75) Inventors: Christine Pagel, Galway (IE); Doreen Seeger, Waldachtal-Tumlingen (DE); Andrew Jeffrey, Tuebingen (DE); Boris Warnack, Mountain View, CA (US); Stefan Leuthold, Zürich (CH); Michael Jetter, Thayngen (CH); Günter Lorenz, Tübingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 240 days.

(21) Appl. No.: 12/093,589

(22) PCT Filed: Nov. 14, 2006

(86) PCT No.: PCT/EP2006/010903
§ 371 (c)(1),
(2), (4) Date: Sep. 17, 2008

(87) PCT Pub. No.: WO2007/054364
PCT Pub. Date: May 18, 2007

(65) Prior Publication Data
US 2009/0036829 A1 Feb. 5, 2009

Related U.S. Application Data

(60) Provisional application No. 60/736,434, filed on Nov. 14, 2005.

(51) Int. Cl.
*A61M 29/00* (2006.01)
*A61M 31/00* (2006.01)
*A61M 37/00* (2006.01)
(52) U.S. Cl. .................. 604/96.01; 604/103; 604/103.12
(58) Field of Classification Search ............... 604/96.01, 604/103, 101.01–101.05
See application file for complete search history.

(56) References Cited

U.S. PATENT DOCUMENTS

| 5,047,045 | A   |   | 9/1991 | Arney et al. |
|---|---|---|---|---|
| 5,156,594 | A   |   | 10/1992 | Keith |
| 5,531,689 | A | * | 7/1996 | Burns et al. ................. 604/99.04 |
| 6,706,010 | B1 | * | 3/2004 | Miki et al. ..................... 604/43 |

FOREIGN PATENT DOCUMENTS

| EP | 1023913 | 8/2000 |
|---|---|---|
| GB | 2372211 | 8/2002 |
| WO | WO2007054364 | 5/2007 |

OTHER PUBLICATIONS

U.S. Appl. No. 60/736,434, filed Nov. 14, 2005, Pagel et al.

* cited by examiner

*Primary Examiner* — Nicholas Lucchesi
*Assistant Examiner* — Rebecca E Eisenberg
(74) *Attorney, Agent, or Firm* — Workman Nydegger (57) ABSTRACT

The present invention relates to a catheter comprising an outer tube; an inner tube; and a balloon fixed at its proximal sleeve to the outer tube and at its distal sleeve to the inner tube, wherein the inner tube comprises an elastic segment.

21 Claims, 9 Drawing Sheets

BALLOON CATHETER WITH ELASTIC SEGMENT

CROSS REFERENCE TO RELATED APPLICATIONS

This application is a §371 Nationalization of PCT/EP2006/010903 filed Nov. 14, 2006 and which claims priority to U.S. Provisional Patent Application No. 60/736,434, filed Nov. 14, 2005, the disclosures of which are incorporated herein by this reference.

BACKGROUND OF THE INVENTION

1. Field of the Invention

The present invention relates to a catheter (1) comprising an outer tube (2); an inner tube (3); and a balloon (4) fixed at its proximal sleeve (5) to the outer tube (2) and at its distal sleeve (6) to the inner tube (3). More specifically, the present invention relates to a catheter with an inner tube (3) comprising an elastic segment (7).

2. Background Information

Non-invasive procedures such as percutaneous transluminal angioplasty (PTA), percutaneous transluminal coronary angioplasty (PTCA), stent delivery and deployment, predilatation before stent placement, postdilatation after stent placement, radiation treatment, delivery of a drug at a lesion site and other procedures are used in the treatment of intravascular disease. These therapies are well known in the art and usually utilize a balloon catheter pushed over a guide wire. After a guiding catheter is placed into the patient's main vessel, a guide wire is advanced in the guide catheter and beyond the distal end of the guide catheter. The balloon catheter is then advanced over the guide wire until it reaches the treatment site at the lesion or stenosis. The balloon is inflated to compress the lesion site and dilate the previous narrowed lesion or stenosis site. If the balloon carried a stent and/or drug, the stent and/or drug is delivered at the site when the balloon is inflated. Likewise, further therapies may also use a balloon catheter for the treatment of the lesion site. Balloon catheters are well known in the art. U.S. Pat. No. 5,047,045 and U.S. Pat. No. 5,156,594 for example describe general concepts of angioplasty catheters.

In PTCA applications, the balloon is usually inflated to pressures higher than the nominal pressure but less than rated burst pressure in order to achieve a slight overdilatation. When the catheter is inflated to pressures higher than the nominal pressure the balloon starts to grow in diameter, but also in length. As the inner tube usually does not grow to the same extend as does the balloon, the inflated balloon tends to bend in one direction. This behaviour is also known as "banana shape effect". On the other hand, once the balloon is inflated and grows, the inner tube being attached to the distal sleeve of the balloon is also forced to stretch itself in the longitudinal direction. This longitudinal growth of the inner tube results in an irreversible and visible over-expansion of the material and results in an "S-shaped" inner tube after deflation of the balloon of the catheter.

SUMMARY OF THE INVENTION

It is therefore an object of the present invention to provide a catheter that does not show a banana-shaped balloon or a s-shaped inner tube. It is further an object of the invention to provide a catheter that is able to prevent the inner tube from being over-expanded upon pressurization of the balloon of the catheter. It is a further object of the present invention to provide an elastic segment that can be integrated into the inner tube of a catheter or constitutes the inner tube of a catheter and allows prevention of banana- or s-shape formation of the balloon or the inner tube during and after inflation of the balloon.

The invention is directed to a catheter (1) comprising an outer tube (2) an inner tube (3) or guide wire tube (3); and a balloon (4) fixed at its proximal sleeve (5) to the outer tube (2) and at its distal sleeve (6) to the inner tube (3), being characterized in that the inner tube (3) comprises an elastic segment (7). The present invention is also directed to an elastic segment of a catheter.

By the provision of an elastic segment that is integrated into the inner tube, the longitudinal growth of the inner tube can be compensated. The elastic segment absorbs the stretching and prevents therewith the inner tube from an over-expansion. When the balloon is deflated, the elastic segment degenerates or contracts itself and thus, the entire inner tube degenerates or shrinks back to its original length and shape.

It is further an object of the present invention to provide a balloon catheter that has an elastic segment but still provides enough push to track the catheter across tight lesions in the vessel. Therefore, the elastic segment preferably shows higher elastic behaviour under pulling forces than under pushing forces and is preferably only elastic in longitudinal direction.

Further advantages and features and embodiments of the present application become apparent from the following detailed description and the description of the drawings.

DETAILED DESCRIPTION OF THE PREFERRED EMBODIMENTS

The catheter and the elastic segment of the present invention have several embodiments described hereinbelow and partly illustrated in the FIGS. 1 through 14. In accordance with the present invention a catheter (1) is provided comprising an outer tube (2); an inner tube (3); and a balloon (4) fixed at its proximal sleeve (5) to the outer tube (2) and at its distal sleeve (6) to the inner tube (3). The catheter further includes an inner tube (3) comprising an elastic segment (7).

Further, in accordance with the present invention an elastic segment is provided that is integrated into the inner tube (3) of a catheter or constitutes the inner tube of a catheter according to the present invention.

Reference will now be made in detail to the present preferred embodiments of the invention.

Figure 1A:
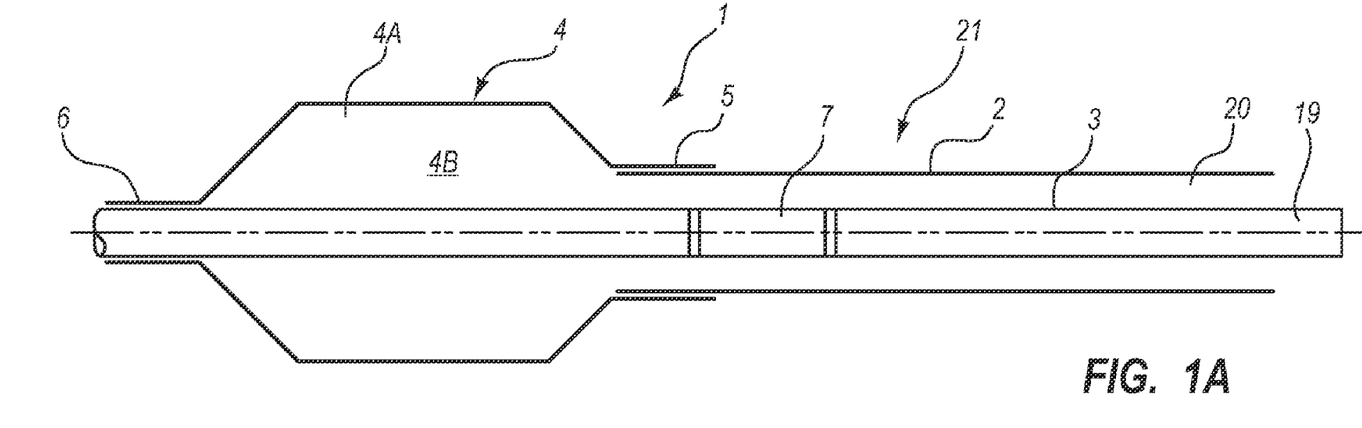
FIGS. 1A and 1B are schematically simplified side views of a catheter according to a first and second embodiment of the invention.
Figure 1B:
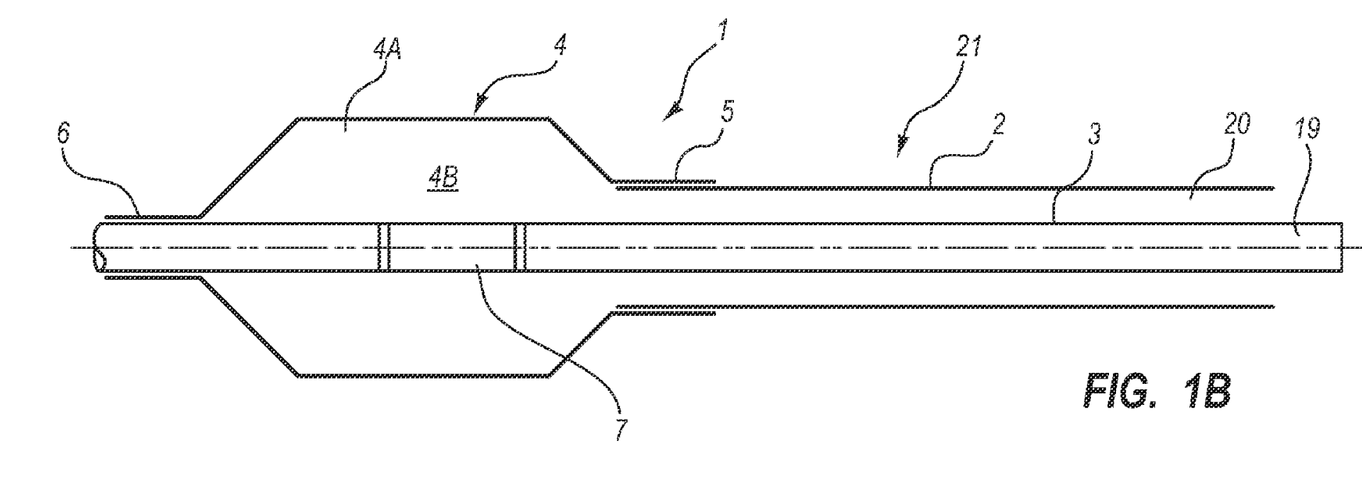

FIGS. 1A and 1B show two embodiments of a distal portion of a catheter (1) comprising an outer tube (2) and an inner tube (3) or also called guide wire tube (3) that is concentrically positioned within the outer tube 2. A balloon (4) comprises a proximal sleeve (5) that is attached to the outer tube 2. Moreover, the balloon (4) comprises a distal sleeve (6) that is attached to the inner tube 3. The balloon (4) furthermore comprises a balloon body 4A defining an interior chamber 4B that can be inflated and deflated by a pressurizing fluid. FIGS. 1 and 2 show the inflated condition of balloon 4. This type of catheter is also referred to as a catheter in a coaxial configuration, i.e. at least in a portion of the catheter proximal of the proximal balloon sleeve, the outer tube is concentrically disposed over the guide wire tube (3) or inner tube (3), the annular space between inner and outer tube creating the inflation lumen, which is in fluid communication with the balloon chamber.

Figure 2A:
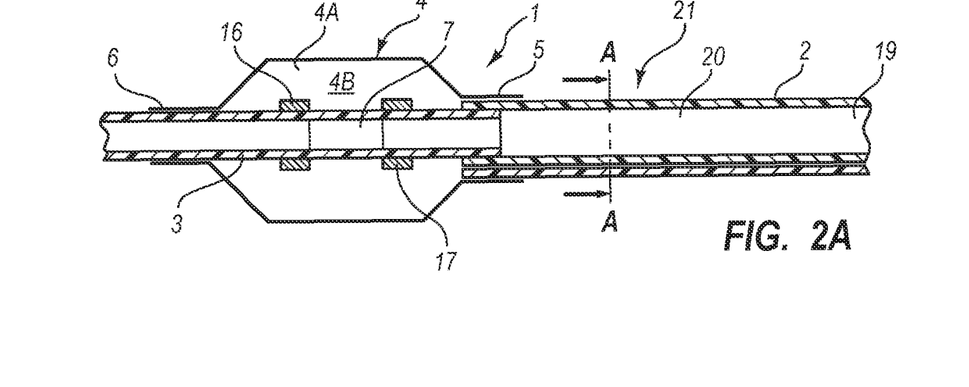
FIG. 2A is a schematically simplified side view of a third embodiment according to the present invention, and FIGS. AB, 2C, 2D, and 2E illustrate possible cross sections taken along line A-A of FIG. 2A.
Figure 2B:
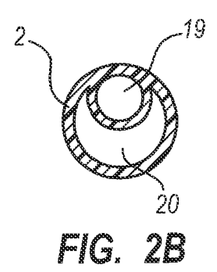
Figure 2C:
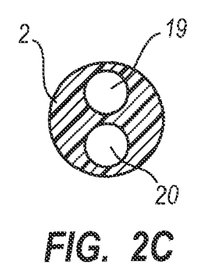
Figure 2D:
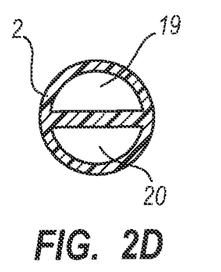
Figure 2E:
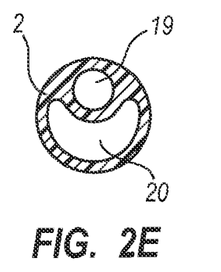

In a further embodiment as shown in FIG. 2A the catheter comprises a catheter shaft (21) in side-by-side lumen configuration, also referred to as dual-lumen catheter shaft. In this configuration the inflation lumen and the guide wire lumen are arranged in a parallel manner to each other, the inflation lumen does not fully surround the guide wire lumen in circumferential direction. Possible cross sections of the catheter shaft construction taken along line A-A in FIG. 2A are shown in FIGS. 2B; 2C, 2D; and 2E. A balloon (4) comprises a proximal sleeve (5) that is attached to the distal end region of the dual-lumen catheter shaft. The distal sleeve (6) of the balloon (4) is attached to the distal region of an inner tube (3), whereby the inner tube (3) itself is in fluid connection to the guide wire lumen. The balloon (4) furthermore comprises a balloon body (4A) defining an interior chamber (4B) that can be inflated and deflated by a pressurizing fluid.

Figure 3:
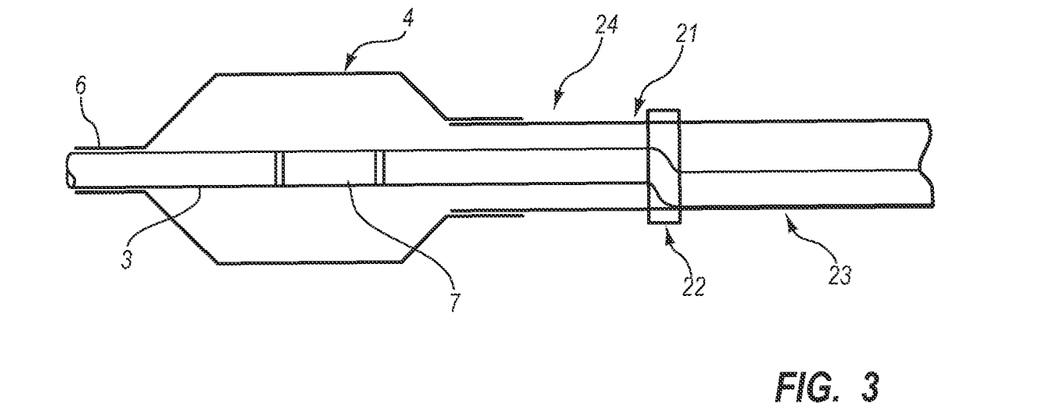
FIG. 3 is a schematically simplified side view of a further embodiment according to the present invention.

In accordance with the present invention, the catheter shaft can also be constructed by a combination of the coaxial shaft design and the side-by-side lumen design. In a preferred embodiment as depicted in FIG. 3, the shaft comprises a proximal portion of the catheter shaft that is configured to have a side-by-side lumen design (24), a transition region (22), and a distal portion proximal of the balloon that is configured to have a coaxial shaft design (23). Such a catheter design is exemplarily described in U.S. Pat. No. 5,370,615 to Johnson.

In accordance with the present invention all embodiments as depicted in FIGS. 1 to 3 comprise an elastic segment (7) that is a tubular component being integrated in the inner tube (3). The embodiment of FIG. 1A shows the elastic segment (7) being positioned in a transitional region between the proximal sleeve (5) and the proximal side of the balloon (4). This depiction is representative of the before-described positioning as well as the positioning underneath the proximal sleeve (5) or at the proximal side of the proximal sleeve (5) of the balloon 4. In turn, FIGS. 1B, 2 and 3 show embodiments according to which the elastic segment (7) is positioned within the interior chamber (4B) of the balloon (4). The elastic shaft segment can have different sizes and lengths in various embodiments. For sake of illustration but not limitation, the elastic shaft segments in FIGS. 1A, 1B, 2 and 3 are indicated as small portions of the inner tube. The elastic segment however can also extend along the whole length of the balloon or a portion thereof. The elastic segment can also constitute the whole inner tube. In case of catheter designs, which have a coaxial catheter construction in their distal shaft portion, the elastic shaft segment can extend from any position distal of the distal balloon sleeve, underneath the balloon sleeve or proximal of the distal balloon sleeve to any position distal, underneath or proximal of the proximal balloon sleeve.

In a first preferred embodiment, the elastic segment (7) is formed of an elastic tubular member (12) integrated into the inner tube (3). The elastic member is more elastic than the balloon. This is achieved by the use of materials for the elastic member having a lower E-modulus than the materials of the balloon (4).

Figure 4A:
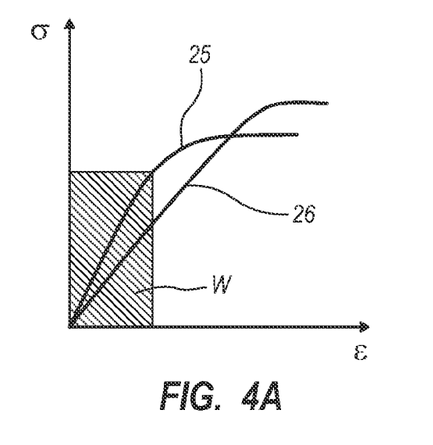
FIGS. 4A and 4B are stress-strain-diagrams of suitable materials for balloon and elastic member according to the present invention
Figure 4B:
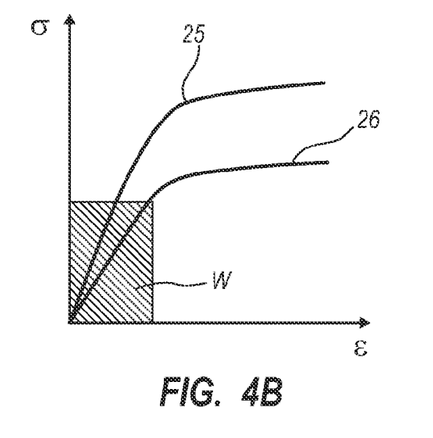

Preferred material characteristics are shown in FIGS. 4A and B, which illustrate stress-strain-diagrams of suitable material combinations for balloon and elastic member. The stress ($\sigma$) is plotted on the Y-axis, while the strain ($\epsilon$) is plotted on the x-axis. Curve 25 indicates the stress-strain-diagram of the balloon material, while curve 26 indicates the stress-strain-diagram of the elastic member. During inflation of the balloon, stress preferably stays in the elastic, i.e. linear region of both curves. Preferred working ranges (W) are indicated by shaded boxes.

Materials suitable for forming the elastic member comprise soft polyesterether block copolymers, e.g. PEBAX 3533, PEBAX 2533, PEBAX 4033, PEBAX 5533, PEBAX 6333, polyurethanes, Silicones, PVC, EVA, Polyethylene, TPE, as well as any polymer classified as having a A-shore hardness, like soft thermoplastic elastomeres. Suitable materials to form the balloon comprise Polyamides (e.g. Nylon 11, Nylon 12, Nylon 6,6), Polyurethanes, Polyetherblockamides (e.g. PEBAX, ELY), Hytrel), PET, and blends and compositions thereof. The inner and outer tube of the catheter can be formed of materials comprising Polyamides (e.g. Nylon 11, Nylon 12, Nylon 6,6, Nylon 7/11, Nylon 11/12), Polyurethanes (e.g. Tecoflex, Pellethene, Bionate, Corethane, Elasteon), Polyethylenes (e.g. PET, PBT, PVDF, ETFE, Teflon), Polyolefins (e.g. HDPE, PE, LDPE, LLDPE, polypropylene), Polyimides, Polyetherblockamides, (e.g. ELY, PEBAX), Polycarbonate blockamides (Ubesta), and blends, compositions or multilayers thereof.

Figure 5:
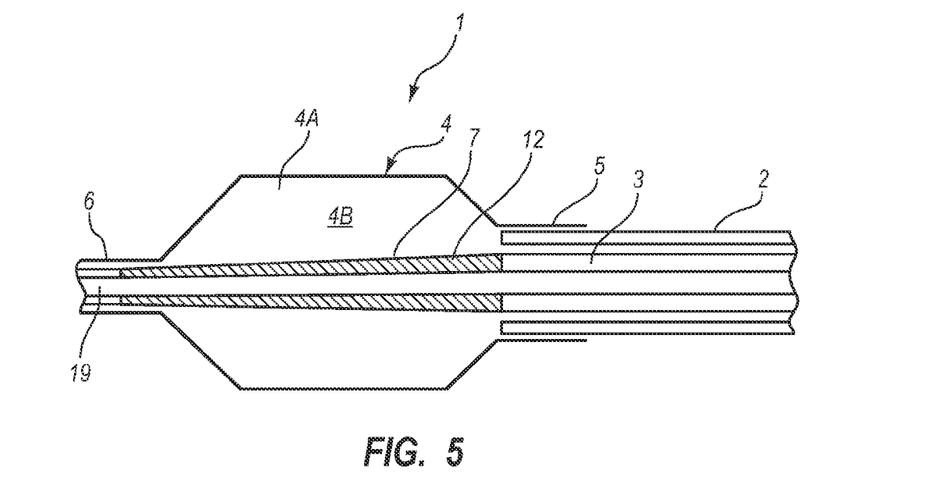
FIGS. 5 and 8 to 15 are schematically simplified side views of alternatives of a catheter according to the present invention.

In one embodiment of the present invention, the elastic tubular member has the same dimensions (i.e. diameter and wall thickness) as does the inner tube. In another embodiment of the preset invention, the elastic tube member has a varying wall thicknesses in order to provide varying flexibility and elasticity to the member. An example is depicted in FIG. 5. In this embodiment the elastic tube member (7, 12) extends from the distal balloon sleeve to the proximal balloon sleeve. The elastic tubular member is tapered from its proximal end to its distal end, e.g., the elastic tubular member is of conical shape. In this example additionally to the provision of an elastic segment, there is also provided more flexibility to the catheter in its distal region.

Figure 6A:
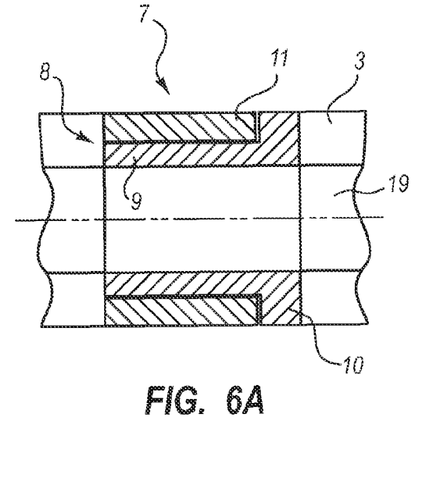
FIGS. 6A, 6B and 7 are schematically simplified side views of alternatives of elastic segments to be used with a catheter according to the invention.
Figure 6B:
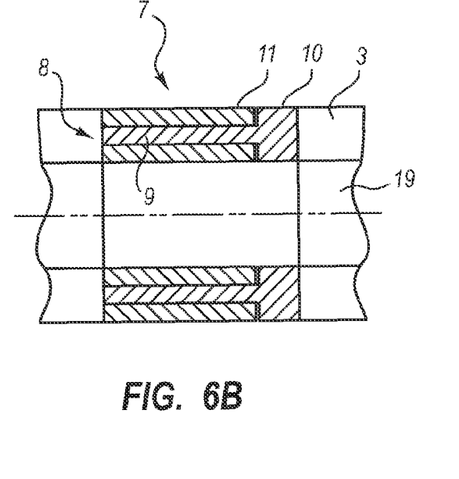

FIGS. 6A and 6B are side views of two options of a further embodiment of the elastic segment (7). Each figure shows a longitudinal cross sectional view of the tubular elastic segment (7) being integrated into the inner tube (3) of the catheter (1). The tubular elastic segment comprises an inner elastic body (8) having a main body portion (9) and a stop portion (10). Both ends of the inner elastic body (8) are fixedly attached to the inner tube (3). The main body portion (9) is surrounded by a sleeve (11) that can be fixedly attached to the inner tube (3) at one end, the other end is loosely abutting the stop portion (10) in order to limit shrinking of the elastic main body portion while for example pushing the balloon catheter through a tight stenosis.

Figure 7:
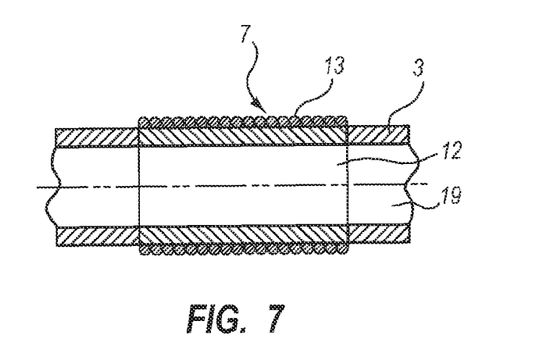

A further alternative embodiment of the present invention is shown in FIG. 7. In this alternative embodiment the elastic segment (7) comprises an elastic element (12) or member (12) that is surrounded or covered by a coil (13) (3) that is wound around at least a portion of the elastic element (12) in a blocked manner so that it is able to restrict the retraction movement of the elastic body (12) (2) upon deflation of the balloon. The coil may cover a portion of the elastic member, the elastic member in its entirety or the coil may also cover portions of the inner tube proximal and/or distal of the elastic member.

Figure 8:
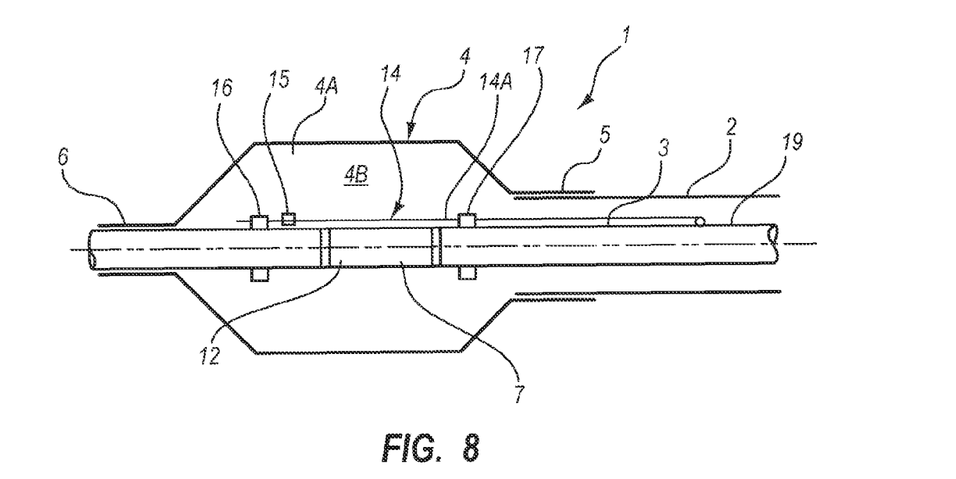

In a further alternative embodiment, the present invention the elastic segment (7) comprises an elastic member (12) and a wire arrangement (14) as depicted in FIG. 8. The wire arrangement comprises a wire (14A) being fixed to the inner tube (3). Wire (14A) is provided with a stop member (15) cooperating with one of markers (15) and (16) positioned on the inner tube (3) in order to limit the contraction movement of wire 14A upon deflation of the balloon 4.

In a further alternative embodiment of the present invention the elastic segment (7) comprises an elastic member (12) and a sleeve (18) covering at least a portion of the elastic member (12).

Figure 9:
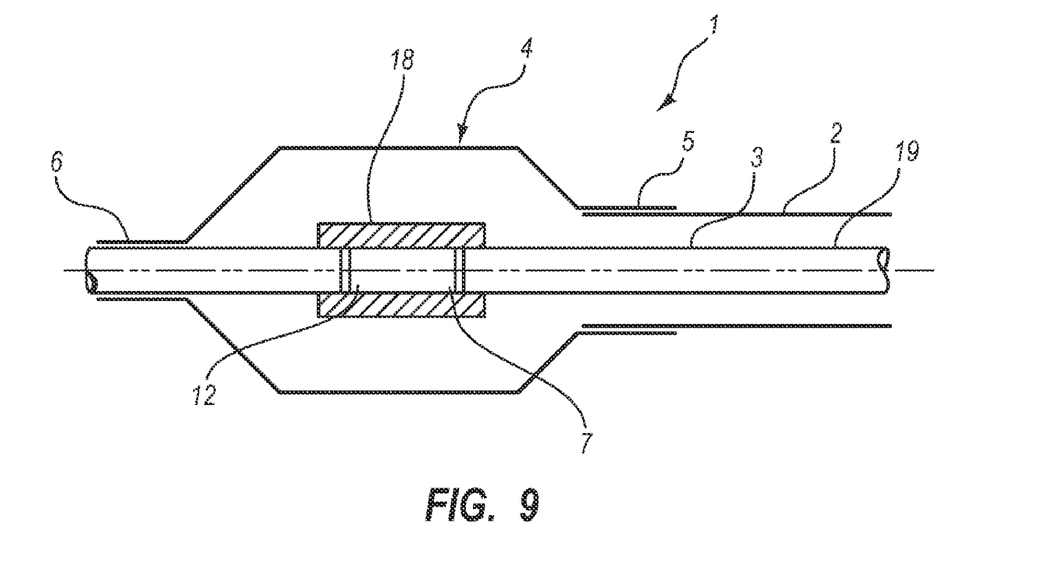

One embodiment is illustrated in FIG. 9 showing the distal portion of a catheter (1) comprising an elastic segment (7) and a sleeve (18) positioned directly on the elastic segment (7). When contracting, the elastic segment (7) is slightly thickened so that, by means of frictional forces, sleeve (18) can restrict the contraction movement of the elastic segment (7).

Figure 10:
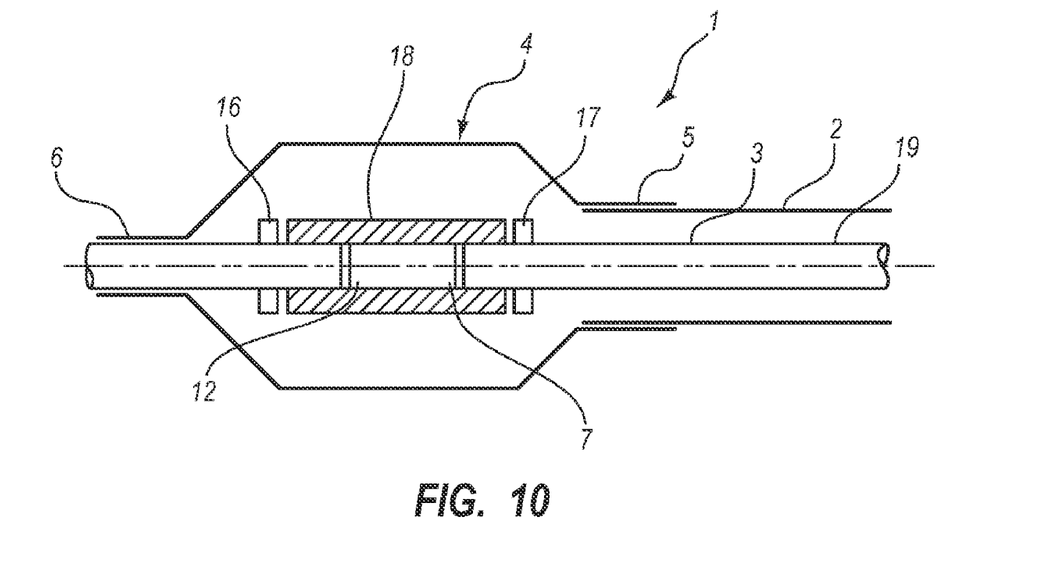

Another embodiment is depicted in FIG. 10. In FIG. 10 there is shown the distal portion of a catheter (1) having an arrangement of a sleeve (18) being positioned on the elastic segment between markers (16) and (17) in order to limit the retraction movement of the elastic segment (7).

Figure 11:
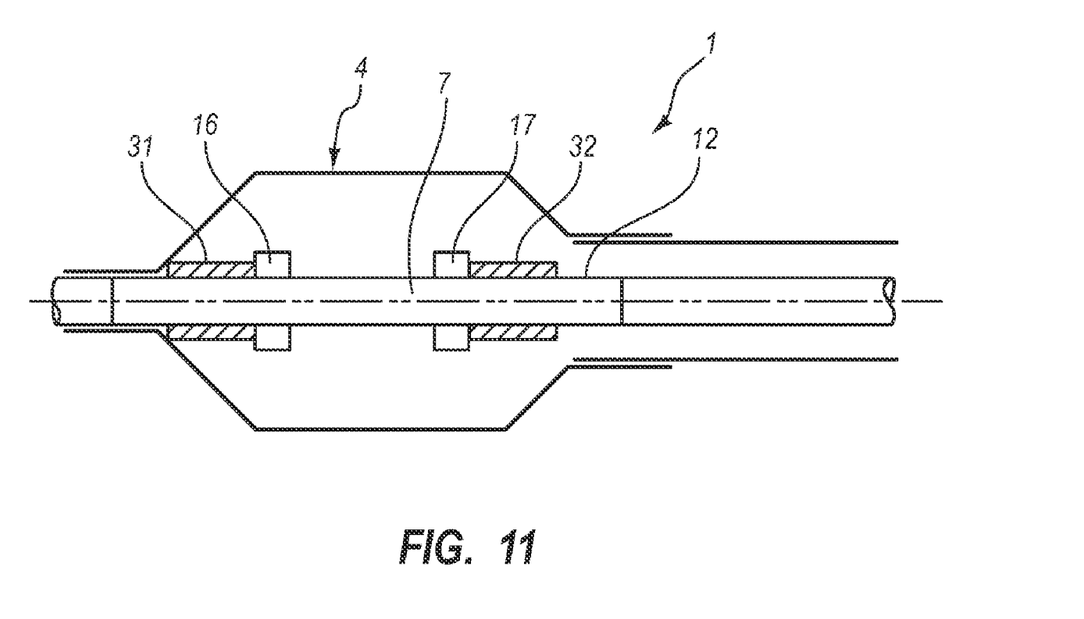

In a further embodiment, rigid shrink tubes made from material with a high E-modulus are mounted on the elastic tube. This way, an elastic segment is created, which has areas of different flexibility and elasticity. FIG. 11 shows the distal portion of a catheter according to the present invention. The elastic member (12) extends along the whole length of the balloon (4). Distal of the distal marker and proximal of the proximal marker a shrink tube (31, 32) is mounted onto the elastic member (12). It is obvious to the person skilled in the art that one or more shrink tube can cover at least one portion but also several portions of the elastic member.

In a further embodiment of the present invention the elastic segment (7) comprises an elastic member and a telescopic inner tube.

Figure 15:
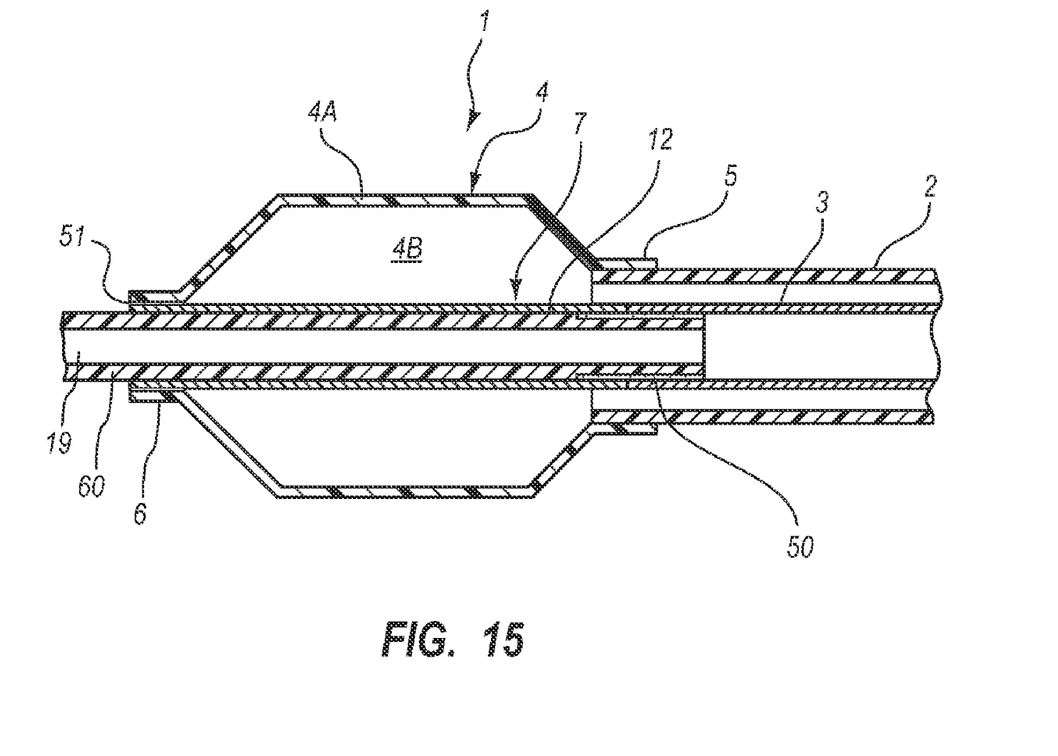

One embodiment according to the present invention is exemplarily shown in FIG. 15. The catheter (1) comprises an outer tube (2) an inner tube (3) and a balloon (4) fixed at its proximal sleeve (5) to the outer tube (2) and at its distal sleeve to the inner tube (3). The inner tube (3) comprises an elastic member (12) that in this example extends from underneath the distal balloon sleeve to a region juxtaposed to the proximal balloon sleeve. However, it is obvious to the person skilled in the art that the elastic member can vary in size and length.

The proximal balloon sleeve is attached to a distal region of the inner tube comprising the elastic member. The elastic segment (7) further comprises a separate shaft member or telescopic inner tube (60) made from material having a lower E-modulus than the material of the elastic member. The separate shaft member (60) is inserted into the inner tube (3) to result in a sliding fit. The separate shaft member (60) is fixedly attached at an attachment site (50) at its proximal end to inner tube (3). The region distal of the proximal attachment side is not fixed to the inner tube nor to the balloon sleeve. By the provision of this telescopic element, the distal balloon end can slide on the separate shaft member (60) upon balloon inflation and deflation, while the separate shaft member will provide push to the catheter tip portion.

In a further embodiment the inner tube consists out of two superposed tubes, a hollow marker shaft tube comprising an elastic member or consisting of an elastic member and a separate distal shaft member tube.

The hollow marker shaft tube is fixed at one end to a proximal tube portion of the guide wire lumen tube and at the other end to the distal balloon sleeve so that said hollow marker shaft tube extends within the interior of the balloon body.

The separate shaft member tube is placed into said hollow marker shaft tube to result in a sliding fit. The proximal end of said separate shaft member is disposed adjacent to the proximal end of the balloon body and is fixed to a proximal inner wall portion of the marker shaft tube, whilst the rest of said separate shaft member is only guided within the hollow marker shaft tube but is not fixed thereto at any other place.

Upon inflation of the balloon, the balloon and the marker shaft tube both elongate, whilst the separate shaft member does not undergo any elongation. This way, the distal end of the balloon end can slide to the distal end of the separate shaft member thus avoiding formation of the banana-shape of the balloon during inflation as well as eliminating the S-shape formation of the inner tube upon balloon deflation.

Figure 12:
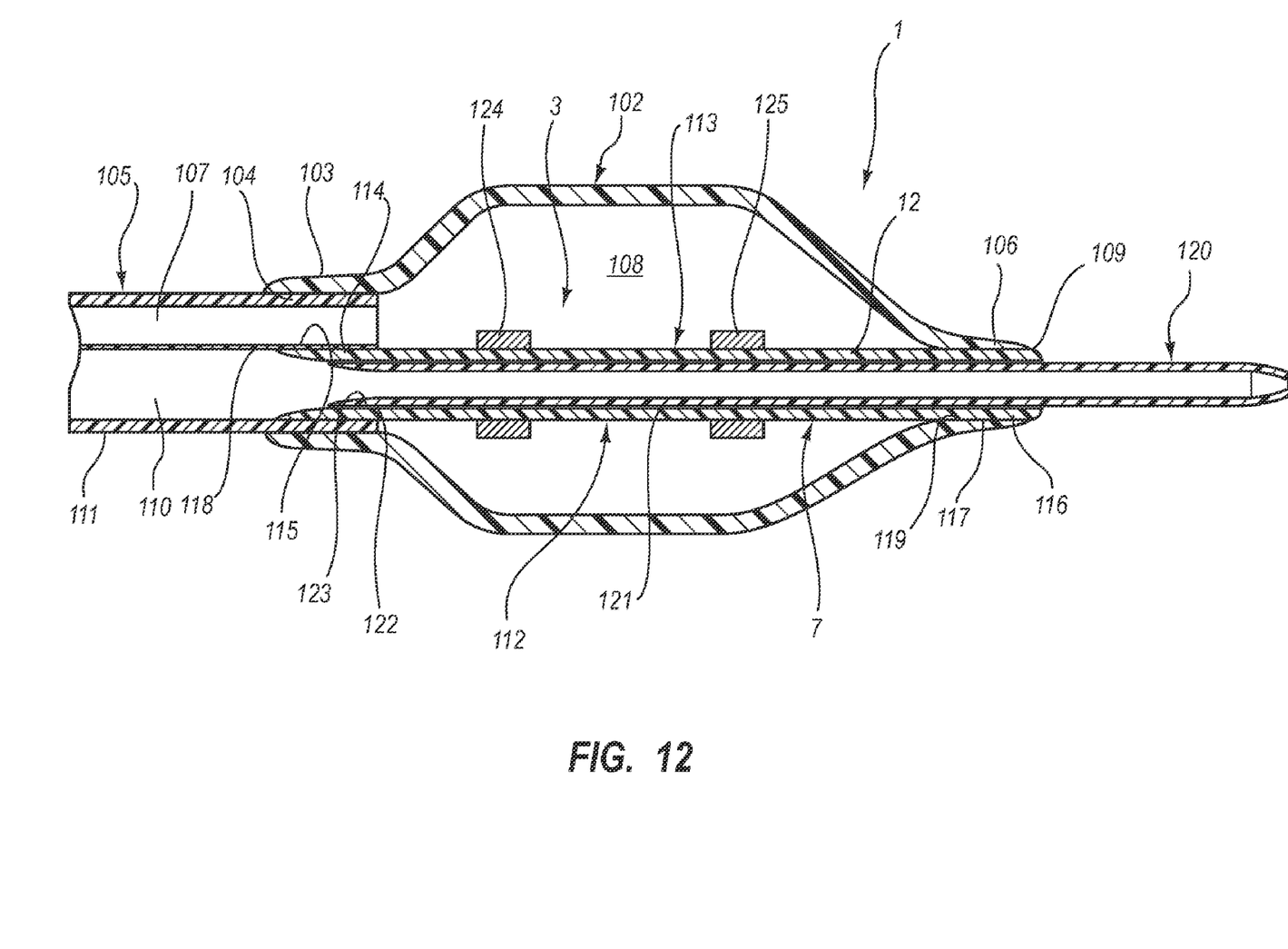

FIG. 12 shows the distal portion of a catheter (1) according to the present invention.

The balloon catheter (1) comprises an inflatable balloon body (102) having a proximal balloon sleeve (103) that is fixed to a proximal end (104) of a catheter shaft (105).

A distal fixing portion (106) of the balloon body (102) is fixed to a distal end region (109) of the inner tube (3).

The catheter shaft (105) includes an inflation lumen (107) that is connected to the interior (108) of the balloon body (102).

Furthermore, the catheter shaft (105) includes a guide wire lumen (110) that is the interior of a proximal tube portion (111), proximal tube portion (111) ending at least approximately (in the present case exactly) at the proximal balloon sleeve (103) of the balloon body (102).

The guide wire lumen (110) extends furthermore into an intermediate tube portion (112) that extends within the interior (108) of the balloon body (102) from the proximal balloon sleeve (103) to the distal fixing portion (106) of the balloon body (102).

Finally, the guide wire lumen (110) extends into a tip portion (120) that extends at least to the distal fixing portion (106). According to the preferred embodiment of FIG. 12, the tip portion (120) extends beyond said distal fixing portion (106), as can be seen from FIG. 12.

The balloon catheter (1) furthermore comprises a hollow marker shaft tube (113) that has a proximal end (114) with an outer circumferential wall (115) and a distal end (116) with an outer circumferential wall (117).

The outer circumferential wall (115) of the proximal end (114) is fixed to an inner wall portion (118) of the proximal tube portion (111). The outer circumferential wall (117) of the distal end (116) of the marker shaft tube is fixed to an inner wall portion (119) of the distal fixing portion (106) of the balloon. The fixation is preferably a weld.

The marker shaft tube (113) carries two marker bands (124) and (125) as can be seen from FIG. 12.

The separate shaft member (121) is loosely fitted into the hollow marker shaft tube (113) and has a proximal end (122) that is fixed to a proximal inner wall portion (123) of said marker shaft tube (113). In one embodiment the separate shaft member (121) is formed from one tube. In another preferred embodiment, the separate shaft member (121) is formed from two tube portions tightly secured together, a proximal intermediate tube portion (112) and a distal tip portion (120).

Figure 13:
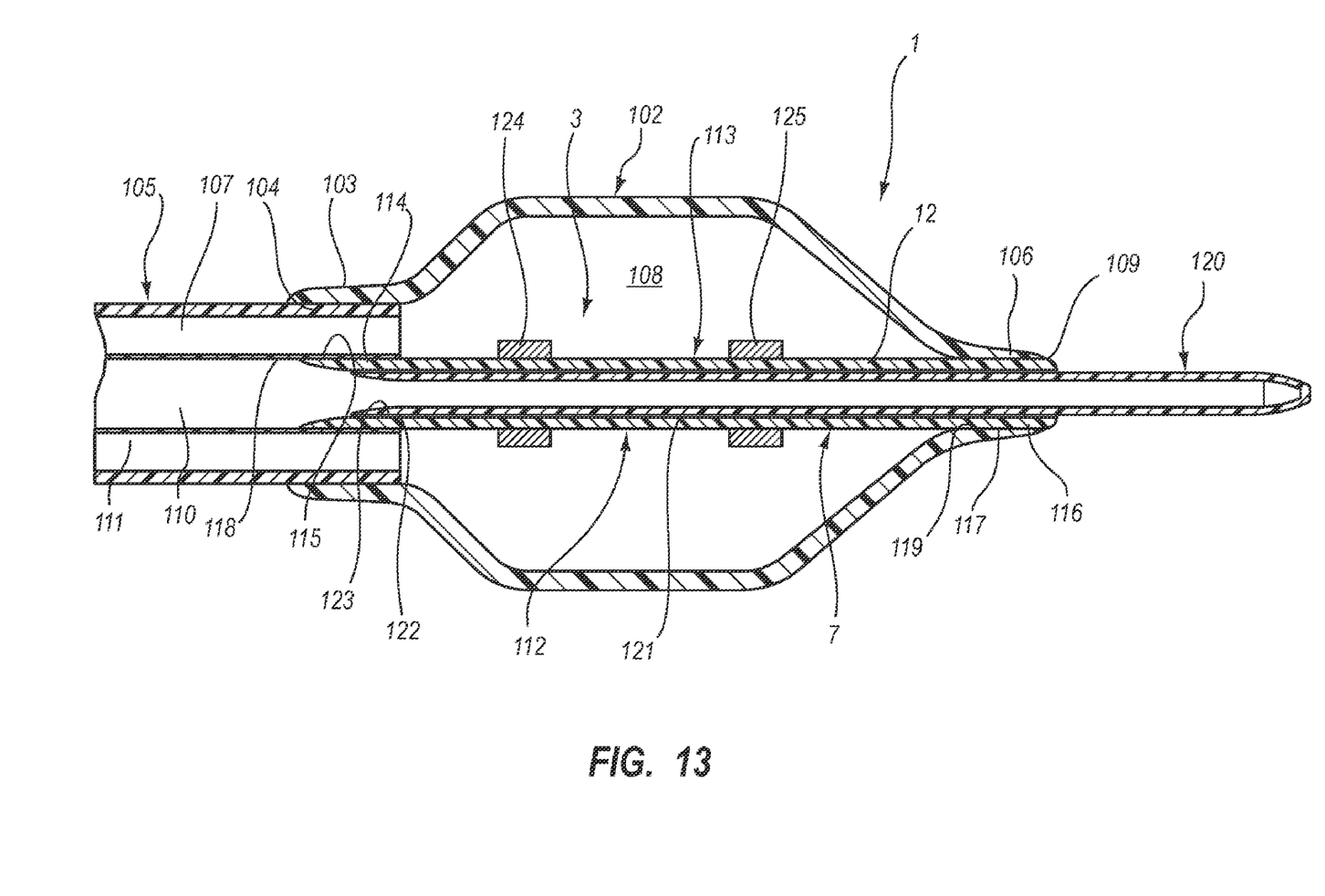

FIG. 13 shows a second embodiment of a balloon catheter that generally corresponds to the embodiment of FIG. 12 so that all parts of said second embodiment are designated with the same reference numerals that were used for the description of FIG. 12.

The difference between the two embodiments is the disposition of the inflation lumen and the guide wire lumen. Whilst the embodiment of FIG. 12 features a juxtaposed positioning of said lumens, i.e. a side-by-side lumen shaft or dual lumen shaft, the embodiment of FIG. 13 includes two concentric tubes comprising the inflation lumen (107) and the guide wire lumen (110), i.e. a coaxial shaft design. One of said tubes is the proximal tube portion (111) that is disposed coaxially within an outer tube (126) so that said two tubes (111) and (126) constitute a part of the catheter shaft (105) of the embodiment of FIG. 13.

In another preferred embodiment of the present invention the elastic segment (7) comprises an elastic tubular member (12) treated with thermal transfer annealing.

Thermal transfer annealing is a method of thermally treatment of thermally responsive material wherein areas in or on the material to be thermally treated are defined and thermal energy is inputted on or into the defined areas in order to change/influence the material characteristics as described in U.S. provisional application No. 60/736,515, which is incorporated herewith herein in its entirety.

It is provided a method of thermal treatment of a thermally responsive material being characterized by (a) defining areas in or on the material to be thermally treated; and (b) inputting thermal energy on or into the defined areas in order to change/influence the material characteristics.

The invention is based on influencing the properties of thermally responsive materials, in particular mechanical characteristics and performance as pushability, kink resistance, flexibility etc. by inputting energy on or into the material in order to re-arrange the morphology and crystallinity in the material structure.

According to the principles of the present invention, the molecular structure of the material can be cross-linked in order to enhance its properties and performance for varying fields of application.

Materials suitable for the elastic member to undergo energy treatment according to the present invention include but are not limited to Polyurethanes (PU) (e.g. Tecoflex, Pellethene, Bionate, corethane, Elasteon, and blends thereof); Polyethylenes (PE) (e.g. PET, PBT, PVDF, Teflon, ETFE, and blends thereof; Polyolefins (e.g. HDPE, PE; LDPE; LLDPE, Polypropylene, and blends thereof); Polyimides; Polyamides; all classes of Nylons (e.g. Nylon 11; Nylon 12; Nylon 6,6; Nylon 6; Nylon 7,11; Nylon 11,12, and blends thereof; Blockcopolymers, PEBA-types (e.g. ELY, PEBAX, Ubesta, and blends thereof; and biodegradable polymers. Also suitable materials are all kinds of blends of the above mentioned materials as well as any composite materials, like duallayers, trilayers and multilayers.

For energy treatment, the elastic member may be placed into an energy source preferably on a mandrel that can for example be coated with PTFE, Polyethylene or polypropylene. The energy source and intensity to be utilized depends on the material to be treated. The term thermal treatment within the scope of this invention includes treatment with various energy sources. The energy sources include but are not limited to wave energy, thermal energy, light energy, laser energy, IR heat, UV light, ultrasound waves and e-beam.

According to the present invention, it is possible to describe any pattern on the outer surface or within the material of the component to be treated, said pattern corresponding to areas that have been defined before the thermal treatment in order to intentionally influence certain regions in or on the material by the thermal treatment. Examples for suitable patterns include but are not limited to spirals with constant or varying pitch, rings, lines, a multiplicity of offset lines, honeycombed patterns as well as any lattice structures.

During the treatment the energy that is inputted in the material or onto the material should be controlled such that the energy does not lead to material ablation from the components to be treated but only delivers sufficient energy to encourage especially cross-linking in the material. The temperature range created by the applied energy preferably includes all temperatures above the glass transition temperature ($T_E$) and all temperatures below the melting temperature ($T_M$) of the material to be treated depending on the storage conditions as well as the water content of the material.

The exact pattern, kind and amount of energy and especially a rotational and/or longitudinal speed and pitch of the component to be treated can be selected according to the desired material characteristics to be achieved.

In a preferred embodiment the polymers to be treated according to the present invention are doped with crosslinking agents in order to adjust the degree of crosslinking upon energy treatment. Crosslinking agents which can be employed include but are not limited to $\alpha,\omega$-olefins; 1,7-Octadiene; 1,9-Decadiene; Trivinylcyclohexane (TVCH); TAIC (Trialylisocyanurate) and related compounds; Pyromellitic acid; Benzophenone teracarboxylic dianhydride (BTDA); Pyromellitic dianhydride (PMDA); Trimesic Acid; 5-Hexene-1-ol; Glycidol; 2-Allylphenol; Diallyl bisphenol-A; 1,3-Phenylene-bisoxazoline; Guanamines; and DYHARD.

In another preferred embodiment the polymers to be treated according to the present invention are doped with nucleating agents or clarifying agents in order to make the polymer more prone to the energy treatment and to be able to further adjust the degree of crystallization of the polymer. Nucleating agents or clarifying agents which can be used include but are not limited to sodium benzoate; Sodium 2,2'-Methylene-bis(4,6-di-tert-butylphenyl) phosphate; Sorbitol-derivatives: para-alkyl substituted methyldibenzylidene Sorbitol; Dibenzylidene Sorbitol; Dimethyldibenzylidene Sorbitol; $\gamma$-Quinacridon; Pimelic acid/Ca-Stearate; N',N'-Dicyclohexyl-2,6-Naphthaline dicarboxamide; Potassium stearate, Sodium benzoate, micronisiated talcum; $Na_2CO_3$; benzoic acid; CaF; Mg-, Ca-, Zn-salts of adipinic acid; Zn-Phenylphosphinate; Zn-Phenylphosphonate; Na-bis(4-tert-butylphenyl)phosphoric acid; Na/Cl-benzoate; Sodium acids of Pyrrol-carboxylates; Dimethyl-4,4'-terephthaloyldioxidibenzoate; 2-Hydroxybenzimidazole; Bis(phenylbromide) methane; and Aluminium hydroxyl-bis(4-tert-butylbenzoate).

Doping of the polymer can be uniform over the polymer article or restricted to certain areas of the polymer article. Further, the amount of the doping agent can vary over regions of the polymer article. One or more doping agents can be used in combination.

The temperature range of the treatment may include all temperatures above the glass transition temperature ($T_E$) and all temperatures below the melting temperature ($T_M$) for a specific water content of the material to be treated, dependent on storage conditions and water content of the material.

It is thus provided a method of treating an elastic member according to the present invention with thermal transfer annealing. It is further provided a catheter according to the present invention comprising an elastic shaft segment manufactured by a process including a step of thermal transfer annealing. Further, an elastic shaft segment is provided, which is manufactured by a process including a step of thermal transfer annealing.

Figure 14:
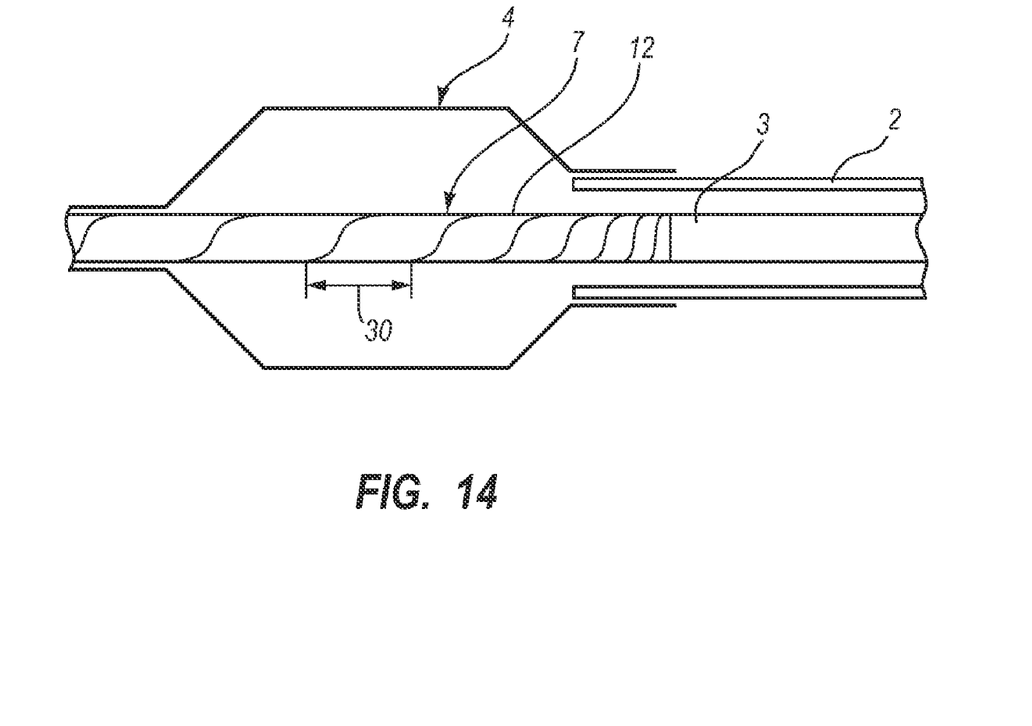

FIG. 14A shows a distal portion of a catheter, comprising an elastic segment (7) featuring a pattern that has been created by inputting energy into the material and influencing thereby the material characteristics. In the present case, the pattern is a spiral with varying pitch, the pitch (30) being increased in distal direction.

By site-specific reinforcement of the elastic tube by thermal transfer annealing according to the present invention, varying characteristics can be added to the elastic member. In order to maintain pushability and trackability of the catheter, varying patterns of reinforced material can be added to the elastic member. Depending on balloon size and length, the ability of the inner tube to stretch and contract can be easily adjusted. Exemplary pattern include but are not limited to spiral reinforcement with constant pitch or varying pitch, offset or staggered straight reinforced lines along the length of the tube, reinforced dots of varying density, chequered reinforcements, or reinforced triangle patterns which taper to the distal portion, By selective reinforcement of tube portions the degree of elasticity and flexibility of the tube can be exactly adjusted to the special needs of the particular catheter and its application.

It will be apparent to those skilled in the art that various modifications and variations can be made in the device of the present invention without departing from the spirit or scope of the invention. Thus, it is intended that the present invention includes modifications and variations that are in the scope of the appended claims and their equivalents.

One skilled in the art would readily appreciate that the present invention is well adapted to carry out the objects and obtain the ends and advantages mentioned, as well as those inherent therein. The devices described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference. The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. A catheter comprising:
an outer tube;
an inner tube disposed within the outer tube, the inner tube comprising an elastic segment, wherein the elastic segment and the inner tube are monolithic, formed as one piece, the elastic segment being formed of a material having a lower e-modulus than the materials forming the inner tube; and
a balloon having a proximal sleeve and a distal sleeve, the proximal sleeve fixed to the outer tube and the distal sleeve fixed to the inner tube, wherein the elastic segment stretches upon inflation of the balloon and contracts upon deflation of the balloon and the inner tube extends uninterrupted from the proximal sleeve to the distal sleeve of the balloon.

2. The catheter according to claim 1, wherein the elastic segment is positioned within the balloon.

3. The catheter according to claim 1, wherein the elastic segment is positioned under the proximal sleeve.

4. The catheter according to claim 1, wherein the elastic segment is positioned proximal of the proximal sleeve.

5. The catheter according to claim 1, wherein the elastic segment is an elastic tube integrated into the inner tube, the elastic segment being formed of a material having a lower e-modulus than the materials forming the balloon.

6. The catheter according to claim 1, wherein the elastic segment includes an elastic inner body and a surrounding sleeve abutting at one end to a stop portion of the elastic inner body.

7. The catheter according to claim 1, wherein the elastic segment includes an elastic inner member and a coil surrounding the elastic inner element.

8. The catheter according to claim 1, wherein the elastic segment includes an elastic member and a wire arrangement with a wire having a stop member, the wire being fixed to the inner tube, the stop member co-operating with at least one marker, of the inner tube.

9. The catheter according to claim 1, wherein the elastic segment comprises an elastic inner member and at least one tube being positioned on the elastic inner element.

10. The catheter according to claim 1, wherein the elastic segment comprises an elastic inner member and a tube being positioned on the elastic inner element said tube being positioned between markers, the markers being positioned on the inner tube.

11. The catheter according to claim 1, wherein at least a part of the elastic segment is thermally transfer annealed.

12. The catheter according to claim 1, wherein the elastic segment further comprises an elastic member and a telescopic tube.

13. A catheter comprising:
an outer tube;
an inner tube including an elastic segment; and
a balloon including:
a proximal sleeve fixed to the outer tube; and
a distal sleeve fixed to the inner tube; and
wherein the elastic segment is part of the inner tube, with the elastic segment constituting a portion of the inner tube, the elastic segment being formed of a material having a lower e-modulus than the materials forming the inner tube; the elastic segment being positioned in a transitional region of the inner tube proximal of the distal sleeve and wherein the elastic segment has an elasticity to compensate for longitudinal growth of the inner tube and the inner tube extends uninterrupted from the proximal sleeve to the distal sleeve of the balloon.

14. The elastic segment according to claim 13, wherein the elastic segment is an elastic tube integrated into the inner tube, the elastic segment being formed of a material having a lower e-modulus than the materials of which the balloon is formed.

15. The elastic segment according to claim 13, wherein the elastic segment includes an elastic inner body and a surrounding sleeve abutting at one end to a stop portion of the elastic inner body.

16. The elastic segment according to claim 13, wherein the elastic segment includes an elastic member and a coil surrounding the inner elastic element.

17. The elastic segment according to claim 13, wherein the elastic segment includes an elastic member and a wire arrangement with a wire having a stop member, the wire being fixed to the inner tube, the stop member co-operating with at least one marker, of the inner tube.

18. The elastic segment according to claim 13, wherein the elastic segment comprises an elastic member and a tube being positioned on the elastic inner element.

19. The elastic segment according to claim 13, wherein the elastic segment comprises an elastic member and a tube being positioned on the elastic inner element the tube being positioned between markers, the markers being positioned on the inner tube.

20. The elastic segment according to claim 13, wherein at least a part of the elastic segment is thermally transfer annealed.

21. The elastic segment according to claim 13, comprising an elastic member and a telescopic tube.

* * * * *